United States Patent [19]
Lau

[11] Patent Number: 5,749,862
[45] Date of Patent: May 12, 1998

[54] CONDOM IMPROVING DEVICE

[76] Inventor: Kai-Ming Lau, Flat B1, 18/F, Block B, 18-26 Kin Wah Street, North Point, Hong Kong, Hong Kong

[21] Appl. No.: 685,030

[22] Filed: Jul. 22, 1996

[30] Foreign Application Priority Data

Aug. 7, 1995 [GB] United Kingdom ............ 6516156
Mar. 8, 1996 [GB] United Kingdom ............ 9605012
Jun. 4, 1996 [GB] United Kingdom ............ 9611632

[51] Int. Cl.⁶ ................... A61F 5/44; A61F 6/04
[52] U.S. Cl. ............... 604/353; 128/844; 128/918
[58] Field of Search ................... 128/842, 844, 128/918; 604/349–353

[56] References Cited

U.S. PATENT DOCUMENTS 4,981,147  1/1991  Barnett .................. 128/844
5,549,120  8/1996  Persson et al. .......... 128/844

*Primary Examiner*—Robert A. Clarke
*Attorney, Agent, or Firm*—Burns, Doane, Swecker & Mathis, L.L.P.

[57] ABSTRACT

A condom improving device in the form of an elastic sheet having an aperture with a cross-sectional area of from 12.5 mm² to 707 mm², the aperture being adapted to receive a condom and the perimeter thereof acting to hold the rim of the condom on the body of a user.

10 Claims, 5 Drawing Sheets

FIG. 4
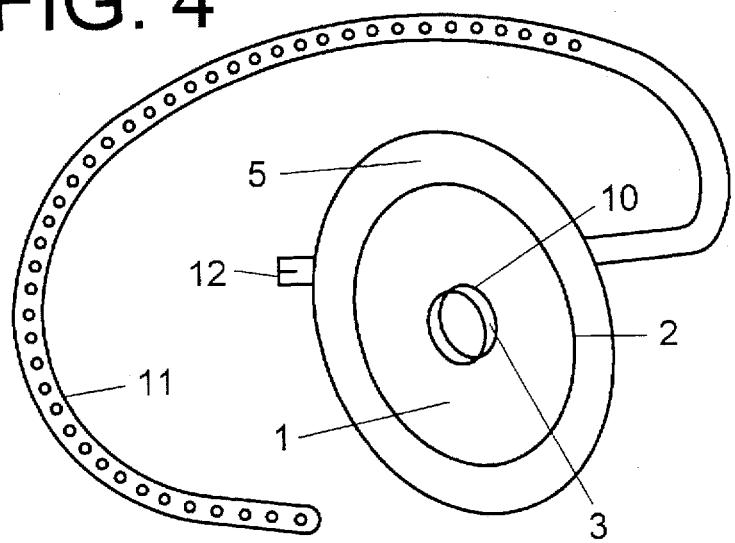
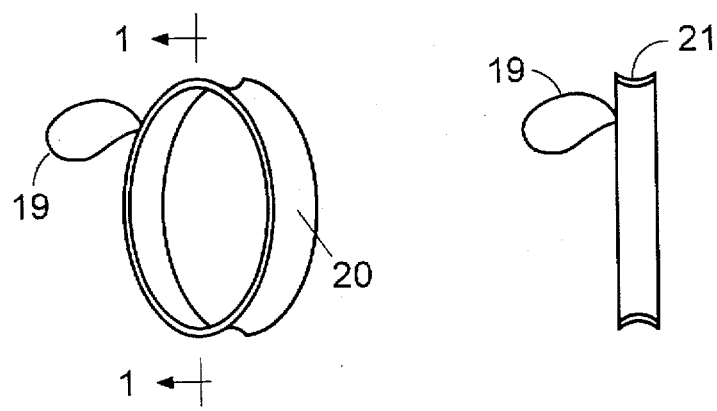
FIG. 5    FIG. 6
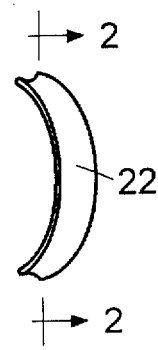
FIG. 7    FIG. 8

5,749,862

CONDOM IMPROVING DEVICE

FIELD OF THE INVENTION

The present invention relates to a condom improving device. In particular, it relates to a device to supplement the use of a condom to improve its function both as a contraception device and as an aid for the prevention of the transmission of diseases.

BACKGROUND OF THE INVENTION AND PRIOR ART

Condoms are well known and widely used in intercourse to reduce the risks of unwanted pregnancy and to mitigate the risk of HIV (AIDS) infection and/or the transmission of other contagious sexually transmitted diseases. Modem condoms are usually made of a highly resilient material such as latex and are stored in the "rolled" form. The open-end of such a condom has a tendency to roll back 3–10 mm and towards the free-end of the penis after it has been unrolled and worn. Thus, in many cases, a condom does not usually cover the whole length of the penis and this potentially can undermine their ultimate effectiveness of the condom. Because of inevitable body contact, virus or bacteria carrying mucus fluid from a persons partner may find its way to reach the penis through the open-end of the condom or when it is removed and cause infection. Also, effective use of a condom means that the penis must be withdrawn soon after ejaculation, possibly against his or his-partner's wishes, to avoid slipping-off of the condom or leakage of semen through the open-end.

Furthermore, the use of a typical condom alone in intercourse obviously can not cover more than the length of the penis which means that scrotum and the area surrounding it would be exposed to vaginal secretions. Also, the use of condoms would not be effective to prevent movements of pubic lice which, though non-fatal, is annoying.

According to the present invention, there is provided a condom improving device comprising an elastic sheet with an aperture there through, wherein the perimeter of said aperture is expandable whereby when a penis wearing a condom is pushed through the aperture until the aperture perimeter reaches or is adjacent the condom rim without passing over it, the aperture is expanded and the perimeter exerts substantially even pressure even the circumstances of the condom to stop semen spilling outside the condom and to stop the condom slipping off the male organ accidentally, wherein the aperture has a cross-sectional area of from 12.5 mm$^2$ to 707 mm$^2$ in the unexpanded state of the perimeter. Preferably, the aperture is substantially circular or elliptical. Preferably, retaining means in the form of a belt, string or band, to hold the device on the user is also provided.

Preferably, the device is provided in combination with an aperture stretcher comprising a complete or partial frame having a curved or straight stretching surface less than 2 cm wide. Preferably, the collar has an internal groove and the frame is circular or substantially circular.

BRIEF DESCRIPTION OF THE DRAWINGS

The present invention will now be described, explained and illustrated, by way of example, and with reference to the following drawings in which:

FIG. 4 shows a third embodiment of the present invention;

FIGS. 5 and 6 shows the perspective and cross-sectional views of a first embodiment of a stretcher for use with the present invention, FIG. 6 being taken along line 1—1 of FIG. 5;

FIGS. 7 and 8 show the perspective and cross-sectional views of a second embodiment of a stretcher for use with the present invention, FIG. 8 being taken along line 2—2 of FIG. 7;

DETAILED DESCRIPTION OF THE INVENTION

Figure 1:
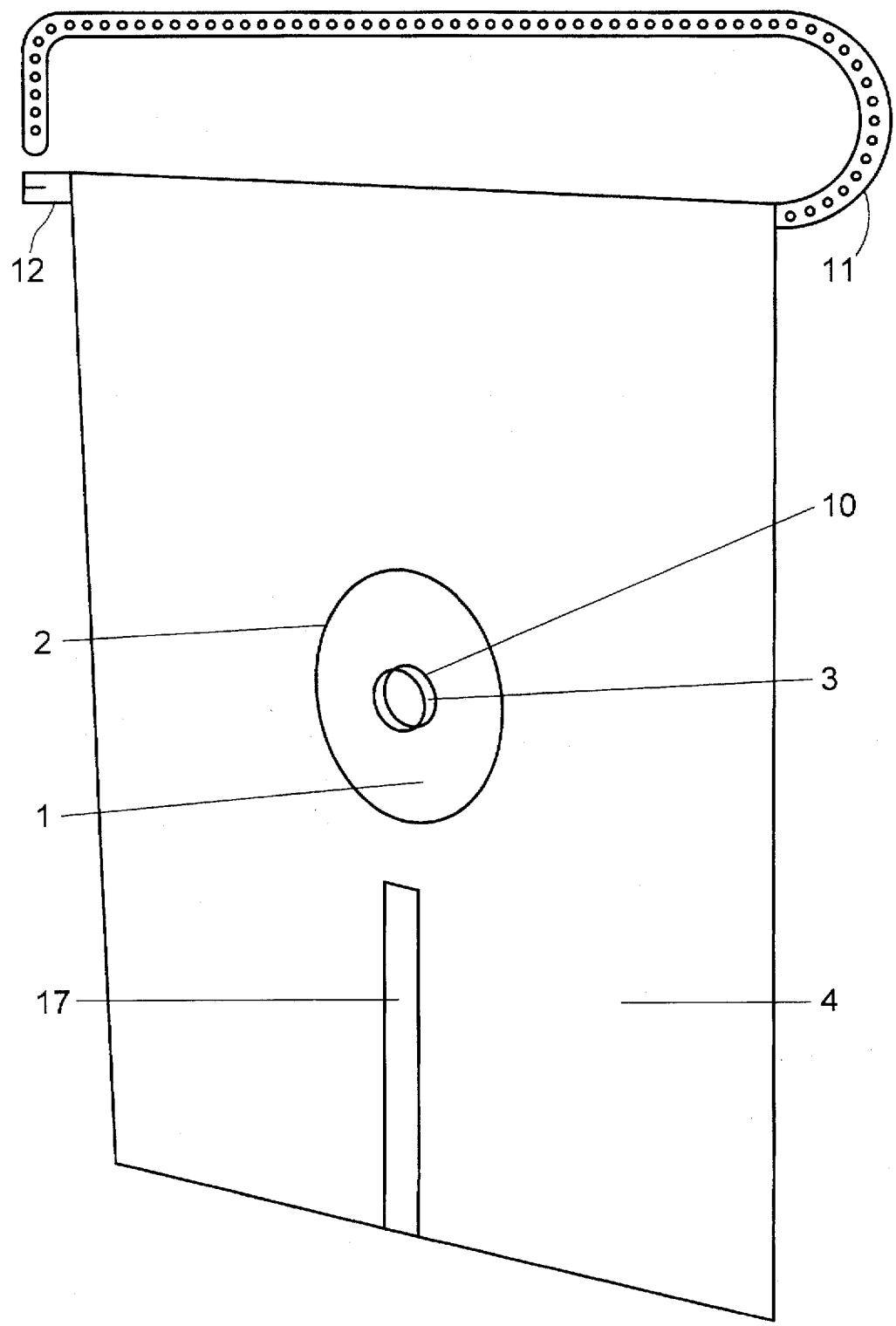
FIGS. 1 and 2 show the front and rear views of the first embodiment of the present invention.
Figure 2:
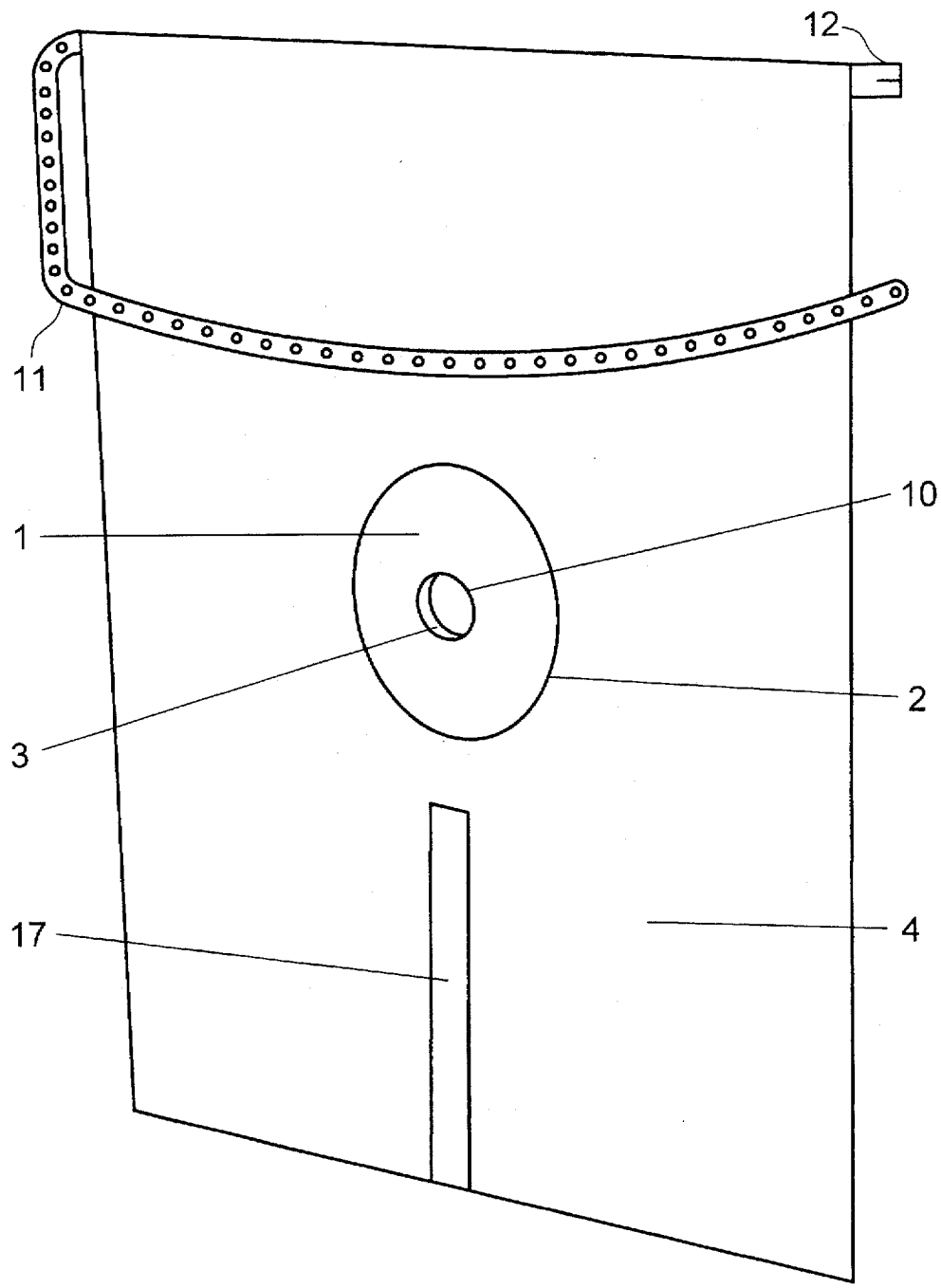
Figure 3:
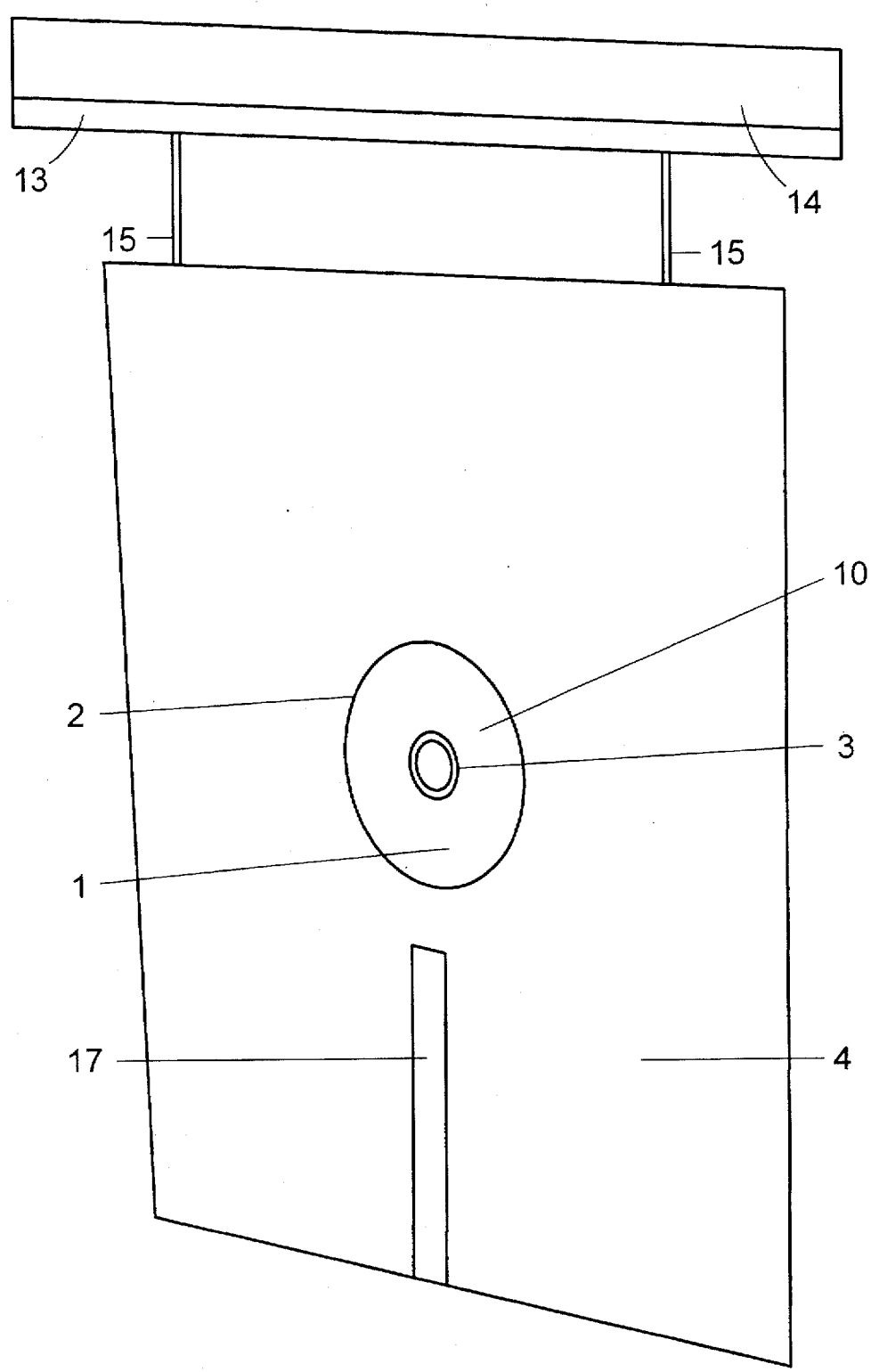
FIG. 3 shows a second embodiment of the present invention.

Referring to the drawings and with particular reference to FIGS. 1 to 3 which show the first and second embodiments of the present invention, the condom improving device of the present invention comprises a sheet 1, an aperture 10 and a collar 3 which surrounds the aperture. The sheet 1 and the collar 3 are preferably made of the same material which is elastic, soft, waterproof and tear-resistant. Latex and balloon rubber are for example ideal. In order to reduce the risk of semen spillage and un-aware or accidental slip-off of the condom after ejaculation or when the end-rim of the condom is loose even during the fully excited state, the collar is resilient so that it is designed to hold the end-rim of a condom firmly onto the base of the penis even when the male organ is in a completely relaxed state.

To effectively hold the condom firmly in position before and after ejaculation, it is desirable that the aperture 10 or collar 3 in its un-stretched state has a smaller dimension than that of a male organ in a state of complete relaxation. To achieve this effect, the aperture 10 could be in the form of a slit so that the narrow sides of the aperture will be mostly stretched. The resilience of the material means that the sides will tend to spring back to their pre-stretched form, thus forming a firm grip which seals and holds the condom in place. However, a slit aperture means that there will be localised uneven resilient stress on the two sides and the collar may still be loose on the two distal ends. The design will have to take this into account and thus a higher compression is required overall which may cause discomfort and hamper blood circulation.

Since a penis usually has a substantially circular, or sometimes elliptical, cross section, it is preferred that the aperture 10 and the collar 3 are also circular so as to closely follow its outline such that the resilient stress is reasonably evenly distributed along the perimeter. While the diameter of a penis of each individual differs according to his age, race and other physical characteristics, it is believed that, because of the strong resilience of the preferred materials, an aperture with a diameter of about 11 mm will be suitable for use by the majority of the population while maintaining a reasonable degree of comfort. It should however be appreciated the diameter of the aperture may lie in the region of 4 mm to 30 mm and still provide a reasonable result. While the aperture 10 on the sheet 1 is preferably circular, it is not essentially so and may be in polygonal forms. Preferably, its area should be in the region of 12.5 mm$^2$ to 707 mm$^2$.

The collar 3 of the present invention is in the form of a flange surrounding the aperture and preferably defining the aperture. It may extend from the surface of the sheet 1 to either or both sides of the sheet. This is provided so that the resilient stress thereon may be evenly distributed over a greater area to secure a better grip and seal. Preferably the axial length of the collar is about 1 mm. It should also be noted that the perimeter of the aperture 10 and collar 3 should be designed in such a way that while the perimeter would exert an adequate pressure on the rim of the condom to prevent un-aware or accidental slip-off and to stop spillage of semen outside the condom when the male organ is in its complete relaxation state after ejaculation, its design must also not cause any obvious discomfort to the user when his organ is at the fully excited state.

The main purpose of the sheet 1 of the device is to provide a shielding in such a way that it stops body secretions and pubic lice from passing through their connection during intercourse. Preferably the sheet 1 is less than 2 mm thick. Ideally, the sheet 1 is less than ½ mm to facilitate adequate elasticity to cope with the biggest and smallest penis volumes without causing discomfort. Naturally, no extra collar is necessary if the thickness of the sheet 1 and the diameter of the aperture are worked out properly to exert proper compression.

To increase the protection area, there is further provided an apron 4 which extends from the resilient sheet 1 to substantially shield the groin area, its neighbouring area or areas where bodily secretions would otherwise appear due to sexual activities. The apron 4 also provides an effective means to reduce the risks of the transmission of pubic lice. Such an apron 4 is preferably made of a soft and waterproof material, such as vinyl or polyester, and could of course be made of the same material as the sheet 1. Furthermore, retaining means 11, 12 are provided on the apron 4 for use on the waist so that it can be properly kept in place.

The retaining means 11 shown in FIGS. 1, 2 and 4 is preferably in the form of an elastic belt 11 which is cheap to manufacture, simple to wear, allows simple adjustment of is tension, easy to unfasten and can be used by both the thinnest and the fattest people. Preferably holes are provided at regular intervals on the belt to allow for people with different waist-lines. If a pointed pin is designed with the buckles, the holes could be eliminated. While the belt is preferably elastic, other non-elastic materials can also be used. The buckle 12 may be made of plastic, metal or other suitable materials. The fixed-pin buckle is preferred since it is simple and cheap. Movable pins may also be used but they cost more to manufacture.

Another possibility is to use adhesive means to retain the device. However, in sexual activities, the apron will be pulled a few cm by the great force of pushing movements and be released repeatedly. If adhesive tape is fixed to the apron as a retaining means for attaching to the user, it is bound to be pulled off repeatedly from the skin. After being re-applied for a few times, it will be covered with skin oil and become useless. Referring to FIG. 3, which shows a second embodiment of the present invention, resilient means such as elastic string 15 is used between the apron 4 and an adhesive tape 14 to be stuck on the abdomen such that the tape 14 will not be pulled off. It is more reliable to use non-adhesive backing sheet 13 with adhesive tape 14. The strip 13 is connected to the sheet 4 by resilient means in the form of two rubber bands 15.

Furthermore, there may be provided a reinforcing strip 17 which is preferably made of the same material as the apron but thicker in order to avoid undesirable deformation, bending or folding of the apron 4. Preferably the strip 17 is about 10 cm long, 4 mm wide and 2 mm thick when the typical apron size is 16 cm×23 cm. A typical distance from the bottom of the apron 4 to the centre of the aperture is about 14 cm. Typical spacing for holes on the belt 11 is about 2.5 cm apart while a typical dimension of the belt is about 92 cm long and 3.5 mm wide. Prior to intercourse a condom is first placed on the penis in the normal manner. The penis is then put through the aperture 10 of the condom improving device with the collar 3, if provided. The apron 4 is held and pulled towards the groin until the aperture 10 nearly reaches the rim, i.e. the remaining rolled-rim portion, of the condom, without passing over it. The retaining means 11, 12 are then fastened around the waist to keep the apron 4 in proper covering position.

In another embodiment, the degree of shielding may be reduced and the apron 4 may not be necessary. Referring to FIG. 4, there is shown a third embodiment of the present invention in which the apron is shrunk to become a small sheet 5, which is provided to assist the user in putting on and removing the device. This embodiment is in all respects the same as the previous embodiments except that it does not cover as effectively the base area of the male organ and the scrotum.

If a male organ, after having been dressed with a condom, is pushed through the aperture 10 of the device, a substantial amount of the lubricant and spermicide which are already present on the outer surface of the condom will be undesirably scraped and moved towards the rolled-rim of the condom. To overcome this problem, there is conveniently provided a stretcher which stretches the aperture 10 of the condom improving device larger to substantially exceed that of the erect male organ before the male organ passes through it. When such a stretcher is fitted in the aperture 10, it resembles a tunnel through which the condom-dressed and erected male organ can pass through the aperture 10 without having its outer surface being scraped by the aperture 10.

An embodiment of the stretcher will now be explained with reference to FIGS. 5 and 6. Referring to the figures, the stretcher comprises a rigid frame, which is substantially circular with an opening substantially exceeding that of a fully excited male organ, made preferably of a non-flexible material such as plastic, wood or even metal. Ideally it should have a sufficient width, e.g. 0.15 to 2 cm, so that when it is fitted or mounted inside the aperture 10 or collar 3 in their highly stretched state, the highly stretched aperture 10 or collar 3 can comfortably rest on the stretcher surface 20. To improve accommodation and retention of the aperture 10, it is preferred that the stretching surface 20 is provided with a groove 21 or an indentation at the middle. Preferably the stretcher is also continuous along its perimeter. To enhance easy handling, the stretcher would have a typical internal diameter ranging from 3 to 9 cm for free passage of the penis of different physical characteristics.

To assist easy removal of the stretcher after the condom improving device has been brought to its proper working place, there is further provided a retrieval means, in this case a loop of string 19 or a tab of fabrics, so that it can be removed from the aperture easily. To provide further convenience to users, the condom improving device may be pre-mounted with a stretcher during production so that the user can simply introduce the pre-mounted device up to the rolled-rim of the dressed condom and then remove the stretcher, thereby positioning the whole device for proper use within a very short time.

A second embodiment of the stretcher is illustrated in FIGS. 7 and 8. The stretcher is a curved frame preferably between 3.5 to 9 cm long with a groove 22 formed thereon for aperture 10 retention purposes. To use this stretcher, the user has to put the stretcher inside the aperture 10 and then stretch the aperture by putting his fingers of his both hands through the concave side of the stretcher and then pull it in the radial manner to enlarge the aperture 10 so that there is sufficient space for the erect organ to pass through. The material for this stretcher is the same as the previous embodiment while its width is preferably between 0.15 and 2 cm. A beneficial aspect of this stretcher is that it could be easily inserted shortly before use so that it does not stretch the aperture too much for too long which may affect the elasticity of the aperture. Even if the stretcher has been pre-mounted in factory and exposed to unfavourable and prolonged storage, such a smaller stretcher will not affect the elasticity of the aperture 10.

Figure 9:
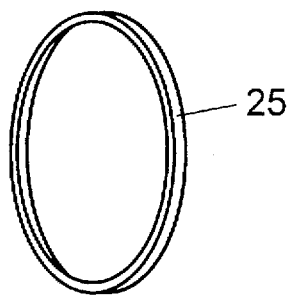
FIG. 9 shows an alternative form of stretcher for the collar.

FIG. 9 shows a further alternative stretcher in the form of a ring which is designed to be fitted into a circumferential groove formed on the inside of the collar 3 and about its axial centre. The stretcher has an outer perimeter significantly larger than that of the aperture 10 in its un-stretched state with a circumferential width which is preferably less than that of the groove so that it can be fitted and retained inside the groove while at the same time providing the aperture 10 with adequate stretching. Its removal could of course be by the use of a suitable retrieval means as mentioned before.

Figure 10:
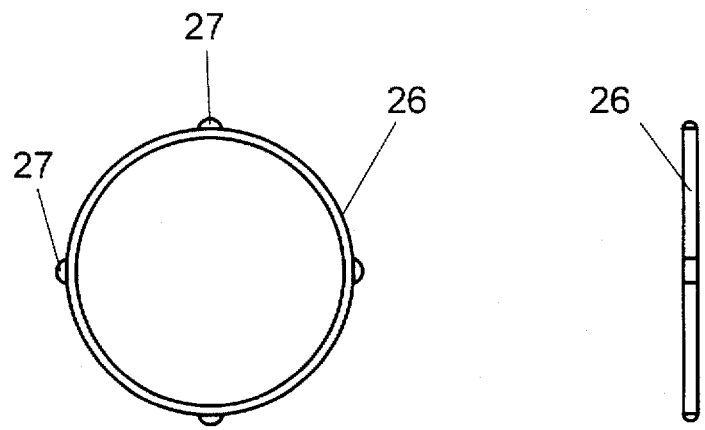
FIGS. 10 & 11 show the front and side views of a further alternative form of stretcher.
Figure 11:
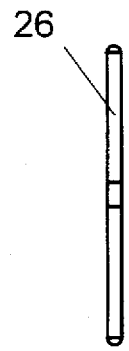

FIGS. 10 & 11 show yet another alternative form of stretcher which has a plurality of protrusions 27 distributed on its circumferential surface 26. The stretcher is to be fitted in a manner similar to that described in the previous embodiments into a collar 3 which has correspondingly shaped recesses for receiving the protrusions.

The stretcher may be substantially circular or elliptical and could have a concave or convex surface instead of the flat surface 25 or protrusions 27 described above. Ideally, the perimeter of the stretcher is less than 28 cm.

What is claimed is:

1. A condom improving device comprising a groin covering panel and a retention means wherein:
   said groin covering panel comprises first and second impermeable sheets;
      said first impermeable sheet being highly elastic and being surrounded by said second impermeable sheet which is substantially non-elastic, and
      said first sheet is provided with an aperture which compressively retains a condom on a penis both in the fully-excited and un-excited states by exerting a substantially radial force on and along the perimeter of said penis and said condom by the resilience of said first impermeable sheet,
      said aperture being expandable between an un-stretched size and a fully stretched size which is defined by the junction between said first and second sheets, and
      said aperture being surrounded by an elastic collar means which is expandable and contractible in response to expansion and contraction of said aperture,
      said collar means comprising an axially extending flange portion which compressively retains said condom on said penis both in the fully-excited and un-excited states by exerting a substantially radial force on and along the perimeter of said penis and said condom by the resilience of said collar means, and wherein
   said retention means comprises means for retaining said condom improving device so that the groin covering panel substantially covers the groin area of an user.

2. The condom improving device according to claim 1 wherein said first sheet is made of a material from the group consisting of latex and balloon rubber.

3. The condom improving device according to claim 1 wherein said retention means is in the form of a belt, string or band, to hold the device on the user.

4. The condom improving device according to claim 1 wherein said aperture is substantially circular or elliptical.

5. The condom improving device according to claim 1 wherein said collar means is integrally formed with said first sheet to complement the pressure exerted by the perimeter of said aperture.

6. The condom improving device according to claim 1 wherein first sheet is made of balloon rubber and said aperture has a un-stretched area from 12.5 $mm^2$ to 707 $mm^2$.

7. A combination of a condom improving device and an aperture stretcher, comprising:
   said groin covering panel comprises first and second impermeable sheets;
      said first impermeable sheet being highly elastic and being surrounded by said second impermeable sheet which is substantially non-elastic, and
      said first sheet being provided with an aperture which compressively retains a condom on a penis both in the fully-excited and un-excited states by exerting a substantially radial force on and along the perimeter of said penis and said condom by the resilience of said first impermeable sheet,
      said aperture being expandable between an un-stretched size and a fully stretched size which is defined by the junction between said first and second sheets, and
      said aperture being surrounded by an elastic collar means which is expandable and contractible in response to expansion and contraction of said aperture,
      said collar means comprising an axially extending flange portion which compressively retains said condom on said penis both in the fully-excited and un-excited states by exerting a substantially radial force on and along the perimeter of said penis and said condom by the resilience of said collar means;
   a retention means for retaining said condom improving device so that the groin covering panel substantially covers the groin area of an user; and
   a removable aperture stretcher, said stretcher having a rigid frame the inner surface of which encloses an opening which is substantially larger than the cross-section of said penis in its fully excited state, and the outer surface of said rigid frame is adapted to removably receive said collar and the perimeter of said aperture.

8. The combination of a condom improving device and an aperture stretcher according to claim 7 wherein said rigid frame is substantially circular or elliptical.

9. The combination of a condom improving device and an aperture stretcher according to claim 7 wherein the outer surface of said rigid frame of said aperture stretcher has a concave profile along its axial length, said concave profile forming a circumferential groove for removably receiving said collar and said perimeter of said aperture.

10. The combination of a condom improving device and an aperture according to claim 7 wherein the outer surface of said rigid frame of said aperture stretcher has an axial length of about 2 cm.

* * * * *